(12) United States Patent
Wachowicz et al.

(10) Patent No.: US 11,589,769 B2
(45) Date of Patent: Feb. 28, 2023

(54) PERIPHERAL TUMOUR TREATMENT

(71) Applicant: ALBERTA HEALTH SERVICES, Edmonton (CA)

(72) Inventors: Keith Wachowicz, Edmonton (CA); Bradley Murray, Edmonton (CA); B. Gino Fallone, Edmonton (CA)

(73) Assignee: ALBERTA HEALTH SERVICES, Edmonton (CA)

( * ) Notice: Subject to any disclaimer, the term of this patent is extended or adjusted under 35 U.S.C. 154(b) by 294 days.

(21) Appl. No.: 16/826,088

(22) Filed: Mar. 20, 2020

(65) Prior Publication Data

US 2020/0229731 A1 Jul. 23, 2020

Related U.S. Application Data

(63) Continuation of application No. 15/040,704, filed on Feb. 10, 2016, now abandoned.

(60) Provisional application No. 62/114,493, filed on Feb. 10, 2015.

(51) Int. Cl.
*A61N 5/10* (2006.01)
*A61B 5/055* (2006.01)

(52) U.S. Cl.
CPC ............ *A61B 5/055* (2013.01); *A61N 5/1049* (2013.01); *A61B 2576/00* (2013.01); *A61N 5/1081* (2013.01); *A61N 2005/105* (2013.01); *A61N 2005/1055* (2013.01); *A61N 2005/1074* (2013.01)

(58) Field of Classification Search
None
See application file for complete search history.

(56) References Cited

U.S. PATENT DOCUMENTS 7,359,535 B2   4/2008  Salla et al.
2009/0003522 A1*  1/2009  Chien .................. A61N 5/1049
                                              378/65

(Continued)

OTHER PUBLICATIONS

Canadian Intellectual Property Office, Office Action received for Application No. 2,920,581, dated Aug. 18, 2022, 4 pages, Canada.

(Continued)

*Primary Examiner* — Hoon K Song
(74) *Attorney, Agent, or Firm* — Alston & Bird LLP

(57) ABSTRACT

A magnetic resonance (MR)-radiotherapy (RT) hybrid system for treating a patient is disclosed. The MR-RT hybrid system comprises: an MR imaging (MRI) apparatus comprising bi-planar magnets configured to generate a magnetic field; a radiation source configured to supply a radiation beam to treat the patient; a gantry configured to couple the MR apparatus at a first end and the radiation source so that they can rotate in unison; a treatment support configured to support the patient; a motor configured to move the treatment support; and a controller. The controller comprises a processor and memory having stored thereon instructions, which when executed by the processor, cause the motor to move the treatment support in order to avoid collision between the MRI apparatus and the patient when the MRI apparatus is rotated. A method for positioning the treatment support within the MR-RT hybrid system is also disclosed.

14 Claims, 4 Drawing Sheets

(56) References Cited

U.S. PATENT DOCUMENTS

| | | | |
|---|---|---|---|
| 2009/0149735 A1* | 6/2009 | Fallone | A61N 5/1049 378/65 |
| 2010/0128838 A1 | 5/2010 | Ayala et al. | |
| 2011/0103668 A1* | 5/2011 | Uchizono | G01R 33/565 382/131 |
| 2015/0209599 A1 | 7/2015 | Schlosser et al. | |
| 2017/0035374 A1 | 2/2017 | Schafer et al. | |

OTHER PUBLICATIONS

U.S. Appl. No. 15/040,704, filed Feb. 10, 2016, Pending.

* cited by examiner

PERIPHERAL TUMOUR TREATMENT

CROSS REFERENCE TO RELATED APPLICATION

The present invention relates generally to hybrid Magnetic Resonance Imaging-Radiotherapy system and specifically to an apparatus and method for peripheral tumour treatment in such a system. This application is a continuation of Ser. No. 15/040,704 filed on Feb. 10, 2016 which claims priority to U.S. Provisional Application No. 62/114,493 filed Feb. 10, 2015. Each of which are incorporated by reference.

BACKGROUND

Most modern radiotherapy (RT) treatments are delivered "isocentrically", where a target volume in a patient is placed at an isocentre of the radiotherapy apparatus. The target volume can then be irradiated from multiple gantry angles without needing to move the patient in order to realign the target volume to the beam axis. The isocentre is often an intersection of a gantry axis and a beam axis of the radiotherapy apparatus. An example of a radiotherapy apparatus is a linear accelerator.

More recently, hybrid magnetic resonance (MR)-RT systems have been used to provide MR guided RT treatments. For example, the systems by ViewRay® and Elekta AB both provide MR guided radiotherapy systems. However for these systems it is difficult, if not impossible, to position the patient so that a peripherally located tumour, such as a breast or lung tumour for example, is at the isocentre without coming into contact with the magnet. This, in turn, reduces the gantry angles from which the tumour may be irradiated thereby inhibiting the effectiveness of the treatment. Accordingly, it is an object of the present invention to obviate or mitigate this disadvantage.

SUMMARY

In accordance with an aspect of an embodiment, there is provided a magnetic resonance (MR)-radiotherapy (RT) hybrid system for treating a patient, the MR-RT hybrid system comprising: an MR imaging (MRI) apparatus comprising bi-planar magnets configured to generate a magnetic field; a radiation source configured to supply a radiation beam to treat the patient; a gantry configured to couple the MR apparatus and the radiation source so that they can rotate in unison; a treatment support configured to support the patient; a motor configured to move the treatment support; and a controller comprising: a processor; and memory having stored thereon instructions, which when executed by the processor, cause the motor to move the treatment support in order to avoid collision between the MRI apparatus and the patient when the MRI apparatus is rotated.

In accordance with another aspect of an embodiment, there is provided a method for positioning a treatment support upon which a patient is positioned within an MR-RT hybrid system, the method comprising: positioning the treatment support at a central location; the central location defined to avoid collision between the patient and the MR-RT hybrid system; rotating a gantry of the MR-RT hybrid system to a gantry angle; moving the treatment support to a treatment position; applying a treatment beam; and moving the treatment support to avoid collision between the MR-RT hybrid system and the patient when the gantry is rotated to a different gantry angle.

BRIEF DESCRIPTION OF THE DRAWINGS

Embodiments of the invention will now be described by way of example only with reference to the following drawings in which.

DETAILED DESCRIPTION OF THE PREFERRED EMBODIMENTS

Figure 1:
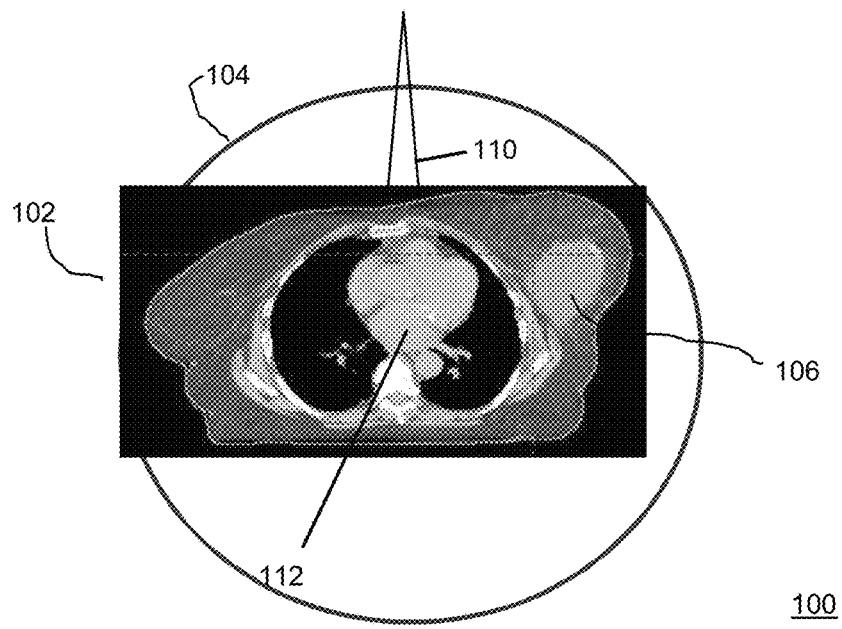
FIG. 1 is a block diagram of a conventional MR-RT hybrid system.

For convenience, like numerals in the description refer to like structures in the drawings. Referring to FIG. 1, a block diagram of a cross-section portion of an MR-RT hybrid system is illustrated generally by numeral 100. The cross-section portion 100 illustrates an image slice of a patient 102 within a magnetic resonance imaging (MRI) apparatus 104. A target volume 106 is peripherally located within the patient 102. In an embodiment, the target volume 106 is a tumour. A radiation beam 110 for treating the tumour 106 passes through the centre of the MRI apparatus 104. Thus, the MR-RT hybrid system 100 has a centrally located isocentre 112. The MRI apparatus 104 used for the MR-RT hybrid system 100 is typically cylindrical and has a bore of approximately 60 cm. An MR-RT hybrid system 100 using biplanar magnets for the MRI apparatus 104 has a similar pole to pole spacing. For patients that are between 50 and 55 cm wide, of which there are many, there is very little room to laterally move the patient 102. Thus, it can be difficult, if not impossible to align the tumour 106 to the isocentre 112 of the MR-RT hybrid system.

In order to allow the MR-RT hybrid system 100 to effectively treat the tumour 106, it is preferable to align the tumour 106 with the radiation beam 110 at all gantry angles. Such an alignment is straightforward for centrally located tumours, but for peripheral tumors, such as breast tumours and lung tumours for example, this would only be possible for the smallest patients. However, the cost to build a magnet with a larger bore or pole-to-pole spacing becomes prohibitively expensive.

Accordingly, a peripheral tumour treatment positioning (PTTP) system and method are described herein. The PTTP system and method allow peripheral tumours in larger patients to be placed at, or proximal to, the isocentre 112 of the MR-RT hybrid system 100 without needing a larger bore or larger pole-to-pole spacing. Thus, the PTTP system and method facilitate treating large patients with peripheral tumours in the MR-RT hybrid system 100.

Figure 2:
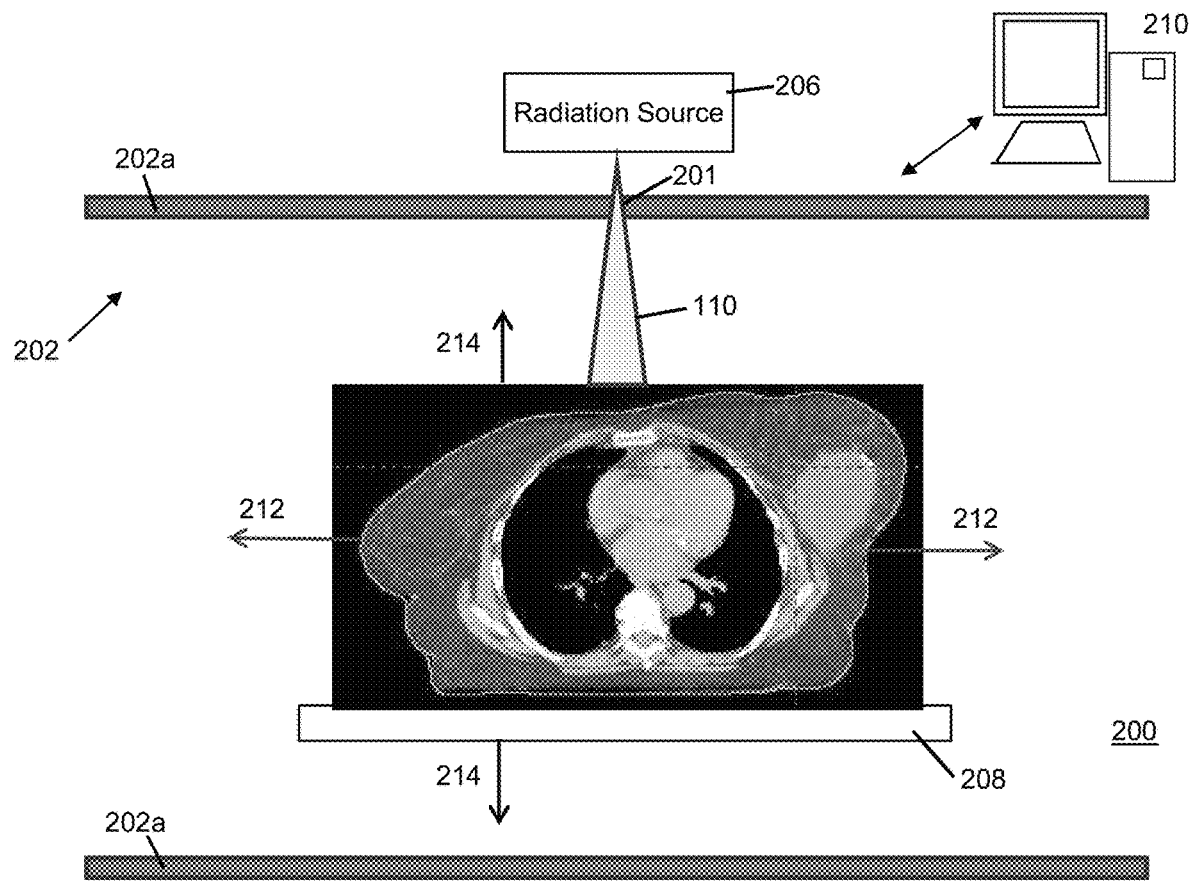
FIG. 2 is a block diagram of an MR-RT hybrid system in accordance with an embodiment of the present invention.

Referring to FIG. 2, a block diagram of an MRI-RT hybrid system in accordance with an embodiment of the invention is illustrated generally by numeral 200. The MRI-RT hybrid system 200 includes an MRI apparatus 202, a rotating gantry (not shown), a radiation source 206, a treatment support 208, and a controller 210. In an embodiment, the treatment support 208 is a couch, table or the like configured to support the patient 102. The MRI apparatus 202 is coupled to the radiation source 206 via the rotating gantry to enable them to rotate in unison about the treatment support 208. An example of such an MRI apparatus is described in U.S. Application Publication No. 2009/0149735, titled "Integrated external beam radiotherapy and MRI system" by Fallone et al. The treatment support 208 is movable by a motor (not shown). Different motors capable of moving the treatment support 208 as described below can be used. In an embodiment, the motor is configured to move the treatment support 208 in a direction parallel to a superior-inferior axis of the patient 102 to move the patient 102 into and out of the MRI-RT hybrid system 200. As is known in the art, the superior-inferior axis runs the length of the patient 102. Further, the motor is configured to move the treatment support 208 substantially any direction normal to the cranial-caudal axis of the patient to position the patient 102 for treatment, as will be described below.

The MRI apparatus 202 is a bi-planar MRI apparatus comprising a pair of spaced apart magnets 202a. The radiation source 206 is directed at the patient 102 either parallel or antiparallel to the direction of the main magnetic field of the MRI apparatus 202 through a hole 201 in the centre of one of the magnets 202a. In the MR-RT hybrid system 200 shown in FIG. 2, the patient 102 is 50 cm wide and the bi-planar magnets have a 60 cm pole to pole spacing.

The bi-planar, space apart, configuration of the magnets 202a allows each magnet 202a to be individually connected to the gantry at a first end only. Such a configuration allows unrestricted lateral motion of the patient 106 in a direction 212 parallel to a face of the magnets 202a, and perpendicular to the radiation beam 110. Such motion is limited in current cylindrical magnets. The bi-planar configuration of the magnets 202a also allows some motion of the patient 102 in a direction 214 parallel to the radiation beam 110, and perpendicular to the face of the magnets 202a.

The controller 210 is a computing device that is configured to control the motion of the treatment support 208. The controller 210 is programmed to position the MRI apparatus 202, the radiation source 206, and the patient 102 so that the target volume 106 is as close to the isocentre of the radiation beam 110 as possible.

Prior to treating the patient using the MR-RT hybrid system 200, a patient centre is determined. The patient centre $(x_c, y_c)$ can be calculated based on an analysis of the contours taken during a simulation process. The analysis determines the patient centre $(x_c, y_c)$ such that a distance from the central point to the skin surface is less than the bore diameter or pole-to-pole spacing of the MRI apparatus 202 for all z positions. Although this analysis could be done from a computed tomography (CT) or MR scan as part of the simulation process, it may be inefficient or unethical, in the case of CT, to scan well above and below the treatment area just to get an external contour for this analysis. Therefore, a method of generating the patient contour from head to toe that does not require a CT or MR could also be used. Devices, such as laser contouring devices, are readily available that could do this in a quick and efficient manner.

Further, a treatment plan is calculated. Specifically, a 3D position of the patient centre $(x_c, y_c, z_c)$ is calculated using contours obtained above. Using techniques similar to conventional isocentric radiotherapy, a 3D location of a pseudo isocentre $(x_{PI}, y_{PI}, z_{PI})$, and gantry angles for each field are defined. In an embodiment, the centre of the target volume is defined as the pseudo isocentre. Based on these two points, treatment centres $(x_T(n), y_T(n), z_T(n))$ are calculated for each gantry angle, where n denotes a radiation beam number. As will be appreciated, since the grantry 204 rotates the MRI apparatus 202 and the radiation source 206 about the patient 102, different gantry angles will likely be associated with different treatment centres. For each of the different gantry angles, the machine isocentre would be relocated to the treatment centre position, and the dose would be calculated. As is well known to those knowledgeable in the art, as the machine isocentre 112 is moved from the pseudo isocentre to the treatment centre, a field size and multileaf collimator (MLC) would need to be adjusted according to divergence. This could be accomplished either manually or through a computerized calculation that adjusted each parameter accordingly. Dose distributions could be calculated and optimized through the various tools normally available in the treatment planning system. If, for any reason, any of the treatment centres needed to be modified as part of the planning process, the system could check that the modified position would be valid and would not cause any collisions.

Figure 3A:
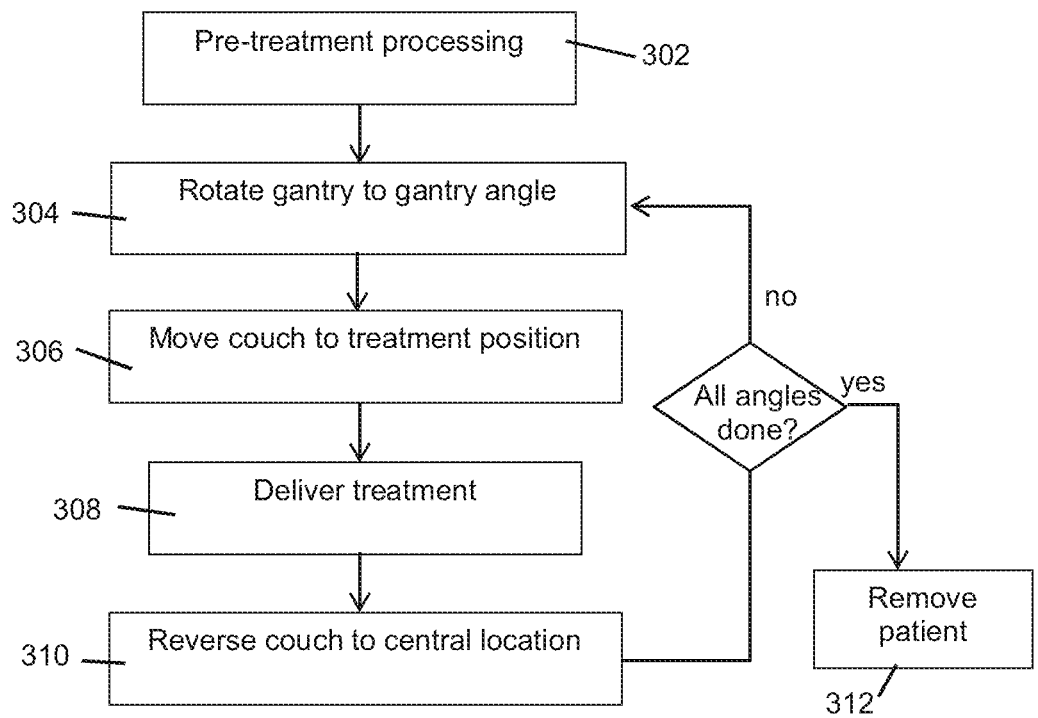
FIG. 3a is a flow chart illustrating operation of the MR-RT hybrid system.

Once the treatment plan has been calculated with the different treatment centres for each radiation beam 110, the patient 102 is ready to be treated with the MR-RT hybrid system 200. Referring to FIG. 3a, a flow chart illustrating operation of the MR-RT hybrid system 200 to position a patient for treatment is illustrated generally by number 300.

Figure 3B:
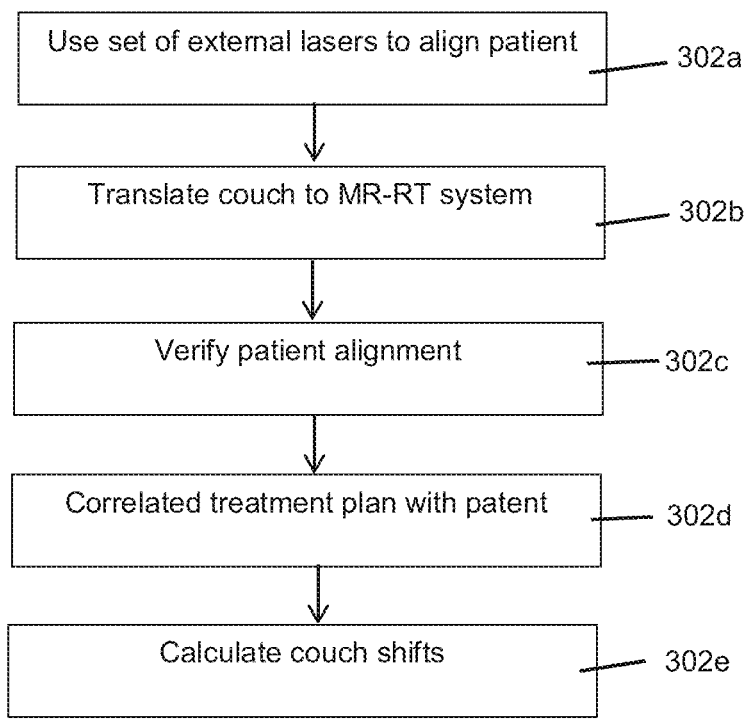
FIG. 3b is a flow chart illustrating pre-treatment processing.

At 302, a pre-treatment process is performed. Referring to FIG. 3b, the pre-treatment process 302 is described in detail. At step 302a, a pre-treatment alignment of the patient 102 is performed to align the patient centre with a central location of the MRI-RT hybrid system 200. In an embodiment, the central location is defined as a position within the MRI-RT hybrid system 200 at which the patient 102 can be placed without fear of contact with the MRI apparatus 202 when the gantry 204 rotates the MRI apparatus 202 and the radiation source 206 about the treatment support 208. In an embodiment, the central location is the isocentre of the MRI-RT hybrid system 200. The patient 102 is positioned at the central location by aligning the patient centre as closely with the isocentre of the MRI-RT hybrid system 200 as possible. Specifically, the patient is positioned by aligning the patient centre to a set of external lasers. Optionally, prior to moving the patient into the MR-RT hybrid system 200, the gantry can be rotated to position the magnets 202a vertically. In this position there will be an opening between the magnets 202a, up to the ceiling. This may minimize the effect of claustrophobia as the patient 102 is moved into the bore of the MR-RT hybrid system 200.

At step 302b, the treatment support 208 is translated a predefined distance from the set of external lasers into the MR-RT hybrid system 200. The predefined distance is configured to correlate the patient centre at the set of external lasers with the isocentre of the MR-RT hybrid system 200.

At step 302c, high quality MR images of an anatomy of interest are taken to verify that the patient centre is accurately aligned to the isocentre of the MR-RT hybrid system 200. If the field of view (FOV) of the MR apparatus 202 is insufficient to obtain a high quality image of the entire anatomy of interest of the patient 102, multiple images can be taken at different treatment support positions and stitched together using known computer graphics techniques. Since most people are wider laterally than they are in the anterior posterior direction, the gantry 204 is rotated to position the magnets 202a horizontally. This configuration allows the treatment support 208 to move laterally sufficiently to obtain a full set of images to stitch together. This configuration also allows the treatment support 208 to be moved so that the pseudo isocentre is aligned with a central axis of the radiation beam 110 and the isocentre MR-RT hybrid system 200 is vertically aligned with the pseudo isocentre.

As a result of the alignment, optimal MR imaging with minimal image distortion is obtained over a central field of view (CFOV) of the MR apparatus 202. Beyond the CFOV, image distortion increases due to gradient non-linearities and magnetic field inhomogeneity. To provide the best image guidance, image-distortion must be minimized. Therefore, vertically aligning the isocentres facilitates optimum quality pre-treatment imaging of the target volume, with the FOV approximately centred on the target volume.

Stitching images obtained at the CFOV for multiple treatment support and/or gantry positions would then allow the creation of a composite image over a larger field of view with the geometric accuracy inherent to the CFOV. Those skilled in the art will recognize that this method of producing an image with minimal distortion would be valuable in the treatment simulation process as well as during pretreatment imaging.

At step 302*d*, once the pre-treatment images are acquired, computer software executing on the controller 210 registers or correlates the pre-treatment images with the MR or CT images used for the treatment planning. This registration could be done using a rigid transformation or a deformable registration, as is known in the art. At step 302*e*, once the two images are registered, the computer software calculates the treatment support 208 shifts, including translations and rotations, needed to align the patient 102 to treatment planning positions. As will be appreciated by a person skilled in the art, in some embodiments the treatment support may be capable of rotating a few degrees to help align the patient 102. Once the shifts have been calculated the treatment support could be translated and rotated by these known amounts to bring the patient centre to the machine isocentre.

After the patient 102 has been aligned using to the pre-treatment image guidance procedure above, the radiation delivery phase can be initiated. At 304, the grantry 204 rotates the MRI apparatus 202 and the radiation source 206 into a first gantry angle for treatment. The initial treatment position is for a first gantry angle, n=1. At 306, the treatment support is translated along a trajectory that moves the patient 102 parallel to the magnets 202 so that the treatment centre $(x_T(1), y_T(1), z_T(1))$ becomes aligned with the isocentre 112 along the beam axis at the first gantry angle. By following this trajectory the patient 102 should not collide with the MR-RT apparatus 202. However, additional known collision avoidance schemes could be used to provide a fail-safe motion trajectory.

Figure 4:
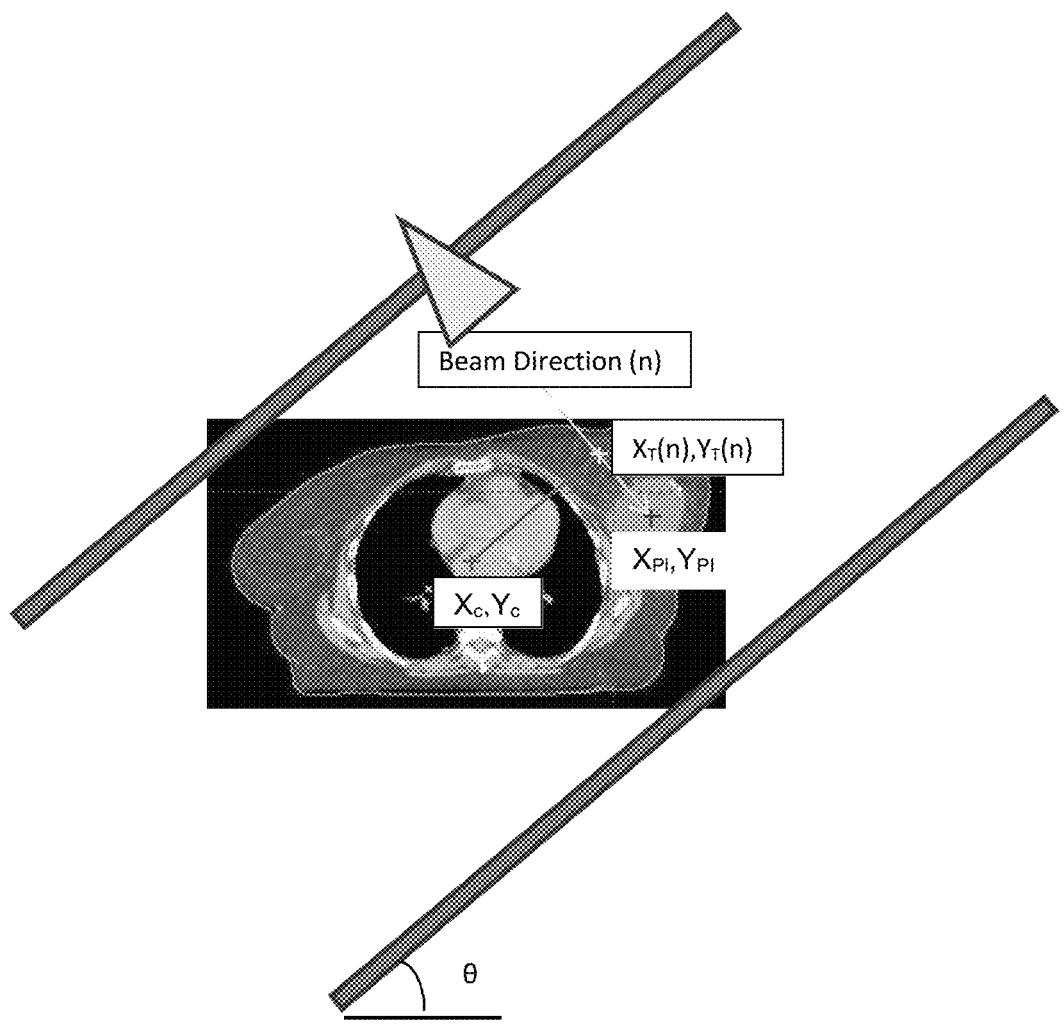
FIG. 4 is a block illustrating the MR-RT hybrid system of FIG. 2 at a different gantry angle.

Referring to FIG. 4, a block diagram of the MRI-RT hybrid system 200 at a gantry angle $\theta$ is illustrated generally by numeral 400. As shown, the patient 102 has been translated so that the target region 106 lies along an axis of the radiation beam 110. Thus, the treatment center $(x_T, y_T)$ is at the intersection of the line from the pseudo isocentre $(x_{PI}, y_{PI})$ to the radiation source 206 and the line perpendicular to it that passes through the patient centre $(x_c, y_c)$. When the treatment center is determined for each gantry angle, the treatment will be similar to an isocentric treatment, in that each radiation beam is pointed towards a common point. In the embodiment, the common point is the pseudo isocentre. However, for each angle, there will be different distances to the patent's skin surface, and from the skin surface to the pseudo isocentre.

At 308, the treatment is delivered. This can be done with MR image guidance before, during or after radiation delivery as desired. At step 310, the treatment support is reversed along the trajectory so that the patient centre is once again aligned with the isocentre of the MR-RT hybrid system 200.

The controller returns to 304 and the the grantry 204 rotates the MRI apparatus 202 and the radiation source 206 into a subsequent position, n=2. The process 304 to 310 repeats until all n radiation beams have been delivered. At step 312, the radiation delivery is complete and the treatment support 208 is translated to remove the patient 102 from the MR-RT hybrid system 200.

As will be appreciated, the MR-RT hybrid system 200 described above provides a controller configured to manipulate the treatment support 108 laterally, vertically and in superior-inferior directions such that a target volume 106*s* is substantially aligned to the radiation beam 110. This may be true even for a peripherally located target volume 106.

Thus, the MRI-RT hybrid system 200 can be used in a number of different circumstance but is particularly useful when the target volume 106 cannot be positioned at or near the isocentre of the traditional radiotherapy apparatus and, as such, an isocentric treatment approach is not typically feasible.

In an alternative embodiment, rather than return the treatment support 208 to the isocentre prior to each rotation of the gantry, the treatment support 208 can be retracted from the MRI apparatus 202. In yet an alternative embodiment, a trajectory can be devised that allows a treatment support and the gantry to move concurrently. Such a trajectory would not require the patient to be moved to either the central location or to be retracted from the MRI apparatus between gantry angles.

Figure 5:
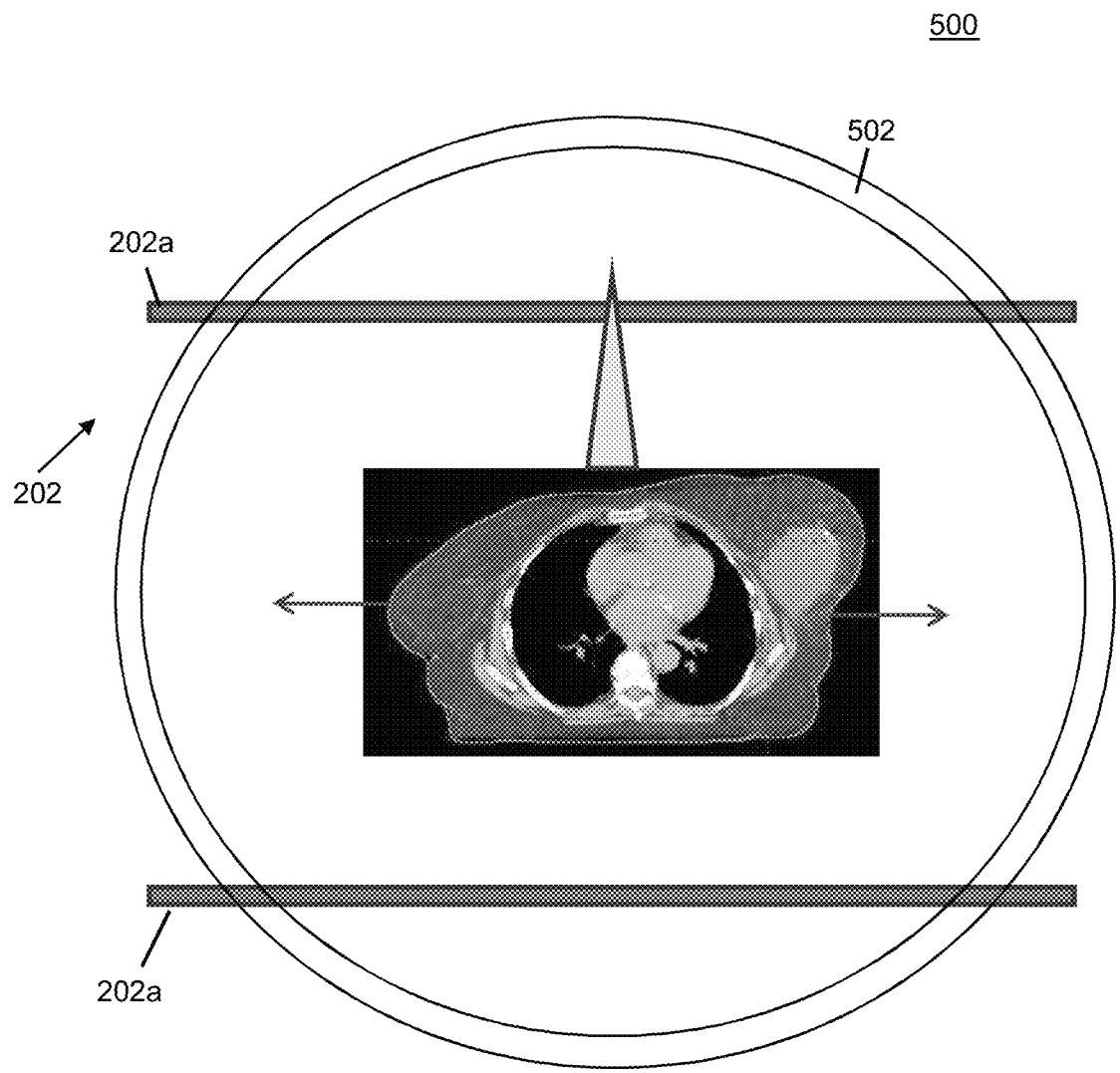
FIG. 5 is is a block diagram of an MR-RT hybrid system in accordance with an alternative embodiment of the present invention.

In the embodiments described above the MRI apparatus 202 comprises a spaced apart bi-planar magnets 202*a*. Depending on the size and configuration of the magnets 202*a*, additional features may be necessary to provide structural support. Accordingly, referring to FIG. 5, an alternative embodiment of the MRI-RT hybrid system is shown generally by numeral 500. Only a portion of the MRI-RT hybrid system 500 is illustrated for simplicity. Specifically, the MRI-RT hybrid system 500 is similar to the previous embodiment but the gantry includes a support structure 502 attached to the magnets 202*a* of the MRI apparatus 202 at an end distal to the first end. In an embodiment, the support structure is an annular flange. Since the annular flange 502 primarily provides structural support, it can have a diameter substantially larger than the pole to pole spacing of the magnets 202*a*.

For example, in an embodiment the pole to pole spacing is 60 cm and the diameter of the annular flange 502 is 110 cm. The diameter of 110 cm is selected based on an average patient size. As will be appreciated, the diameter of the annular flange 502 can be larger to accommodate a larger average patient size. Accordingly, although the support structure 502 is described as an annular shaped flange having a particular size, it will be appreciated that other shaped and sized flanges may also be used to provide structural support to the MRI apparatus 202.

The annular flanges 502 may inhibit motion of treatment support 208 if a portion of treatment support 208 is positioned outside of the MRI apparatus 202. However, because the opening of the annular flange 502 is significantly larger than the pole to pole spacing, it will allow substantial motion of the patient support 208. Further, if the entire treatment support can be positioned within the MRI apparatus 202 then the annular flange 502 may not affect motion of the treatment support 208 at all.

Although preferred embodiments of the invention have been described herein, it will be understood by those skilled in the art that variations may be made thereto without departing from the scope of the appended claims.

The invention claimed is:

1. A magnetic resonance (MR)-radiotherapy (RT) hybrid system for treating a patient, the MR-RT hybrid system comprising:
    an MR imaging (MRI) apparatus comprising bi-planar magnets configured to generate a magnetic field;
    a radiation source configured to supply a radiation beam to treat the patient;
    a gantry configured to couple the MRI apparatus at a first end and the radiation source so that they can rotate in unison;
    a treatment support configured to support the patient;
    a motor configured to move the treatment support; and
    a controller comprising:
        a processor; and
        memory having stored thereon instructions, which when executed by the processor, cause the motor to:
            move the treatment support in order to avoid collision between the MRI apparatus and the patient when the MRI apparatus is rotated: and
            move the treatment support to a central location within the MR-RT hybrid system prior to rotation of the MRI apparatus to position a patient center substantially in alignment with an isocenter of the MR-RT hybrid system and then move the treatment support to at least one treatment position within the MR-RT hybrid system to position a center of a patient target volume substantially in alignment with the isocenter of the MR-RT hybrid system.

2. The MR-RT hybrid system of claim 1, wherein, for each gantry angle, the instructions, when executed by the processor, cause the motor to firstly move the treatment support to the central location prior to rotation of the MRI apparatus and to secondly move the treatment support to the treatment position.

3. The MR-RT hybrid system of claim 2, wherein the gantry is configured to rotate to each gantry angle only when the patient is at the central location.

4. The MR-RT hybrid system of claim 1, wherein the radiation beam is focused at the isocenter of the MR-RT hybrid system.

5. The MR-RT hybrid system of claim 4, wherein in the treatment position, the patient target volume is aligned with the isocenter along a beam axis of the radiation source.

6. The MR-RT hybrid system of claim 1, wherein the gantry further comprises a support structure connecting the bi-planar magnets distal from the first end, the support structure having an opening larger than a pole to pole spacing of the bi-planar magnets.

7. A method for positioning a patient treatment support within an MR-RT hybrid system, the method comprising:
    (i) positioning the patient treatment support at a central location within the MR-RT hybrid system defined to avoid collision between a patient positioned on the patient treatment support and the MR-RT hybrid system, and to align substantially a center of the patient with an isocenter of the MR-RT hybrid system;
    (ii) rotating a gantry of the MR-RT hybrid system to a gantry angle;
    (iii) moving the patient treatment support from the central location to a treatment position to align substantially a center of a patient target volume with the isocenter of the MR-RT hybrid system;
    (iv) applying a treatment beam to the patient;
    (v) returning the patient treatment support to the central location; and
    (vi) repeating steps (ii) to (v) for each subsequent gantry angle to which the gantry is rotated thereby to avoid collision between the MR-RT hybrid system and the patient positioned on the treatment support at each gantry angle.

8. The method of claim 7, wherein the patient treatment support is moved concurrently with rotation of the gantry to avoid collision.

9. The method of claim 7, further comprising focusing the treatment beam at the isocenter of the MR-RT hybrid system.

10. The method of claim 9, wherein moving the patient treatment support to the treatment position aligns the patient target volume with the isocenter along a beam axis of the MR-RT hybrid system.

11. The method of claim 7, wherein the gantry is only rotated when the patient is at the central location.

12. The method of claim 7, wherein the center of the patient is determined using contour analysis prior to positioning the treatment support at the central location.

13. The method of claim 12, wherein MR imaging is used to confirm that the center of the patient is correctly aligned with the isocenter prior to an initial rotation of the gantry.

14. A non-transitory computer readable medium having stored thereon executable instructions for positioning a treatment support upon which a patient is positioned within an MR-RT hybrid system, the instructions when executed by a processor, causing the MR-RT hybrid system to:
    (i) position the treatment support at a central location within the MR-RT hybrid system defined to avoid collision between the patient positioned on the treatment support and the MR-RT hybrid system, and to align substantially a center of the patient with an isocenter of the MR-RT hybrid system;
    (ii) rotate a gantry of the MR-RT hybrid system to a gantry angle;
    (iii) move the treatment support to a treatment position to align substantially a center of a patient target volume with the isocenter of the MR-RT hybrid system;
    (iv) apply a treatment beam to the patient;
    (v) return the treatment support to the central location; and
    (vi) repeat steps (ii) to (v) for each subsequent gantry angle to which the gantry is rotated thereby to avoid collision between the MR-RT hybrid system and the patient at each gantry angle.

* * * * *